United States Patent [19]

Saari et al.

[11] 4,376,772
[45] Mar. 15, 1983

[54] USE OF PIPERAZINYL-IMIDAZO[1,2-A]PYRAZINES IN SEDATION

[75] Inventors: Walfred S. Saari, Lansdale; Joel R. Huff, Gwynedd, both of Pa.

[73] Assignee: Merck & Co., Inc., Rahway, N.J.

[21] Appl. No.: 328,894

[22] Filed: Dec. 9, 1981

[51] Int. Cl.$^3$ ................ A61K 31/195; A61K 31/495; A61K 31/505

[52] U.S. Cl. .................................. 424/250; 424/251; 424/319

[58] Field of Search .................... 424/250, 251, 319

[56] References Cited

U.S. PATENT DOCUMENTS 4,078,063  3/1978  Lumma et al. .................. 424/250
4,081,542  3/1978  Lumma et al. .................. 424/250
4,082,844  4/1978  Lumma et al. .................. 424/250
4,242,344 12/1980  Lumma ............................. 424/251

FOREIGN PATENT DOCUMENTS 817608  1/1975  Belgium.

OTHER PUBLICATIONS

Birch et al., Br. J. Pharmacol., 68, 107p (1979).
Drew et al., Br. J. Pharmacol., 67, 133 (1979).
Clineschmidt et al., Arch. Int. Pharmacodyn. Ther., 244, 231 (1980).
Autret et al., Eur. J. Pharmacol., 12, 319 (1977).

*Primary Examiner*—Stanley J. Friedman
*Attorney, Agent, or Firm*—William H. Nicholson; Mario A. Monaco

[57] ABSTRACT

Piperazinyl-imidazo[1,2-a]pyrazines and their acid addition salts are selective $\alpha_2$-adrenergic receptor antagonists and are thereby useful for treating sedation caused by antihypertensive drug therapy.

7 Claims, No Drawings

USE OF PIPERAZINYL-IMIDAZO[1,2-A]PYRAZINES IN SEDATION

BACKGROUND OF THE INVENTION

This invention is concerned with a novel method of treating antihypertensive agent-induced sedation by the administration of piperazinyl-imidazo[1,2-a]pyrazines of general structure I which are selective $\alpha_2$-adrenergic receptor antagonists.

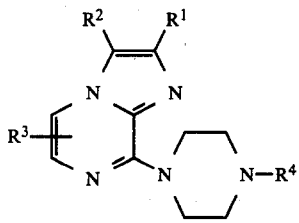

The piperazinyl group is particularly ubiquitous among compounds with useful pharmacological properties. Piperazinylpyrazines (U.S. Pat. Nos. 4,081,542 and 4,082,844), piperazinylquinoxalines (Belgian Pat. No. 817,608), 2-piperazinyl-5 (and/or 6)-substituted pyridines (U.S. Pat. No. 4,078,063) and piperazinyl-imidazo[1,2-a]pyrazines (U.S. Pat. No. 4,242,344), the compounds useful in the novel method of treatment of this invention, are known anorexigenic agents which are also said to have antidepressant activity by virtue of their pharmacological influence on serotonin levels.

Now, with the present invention there is provided a novel method of treating antihypertensive anti-induced sedation by the administration of these piperazinyl-imidazo[1,2-a]-pyrazines, which are $\alpha_2$-adrenergic receptor antagonists.

Sedation, a limiting side effect produced by some antihypertensive agents, is associated with stimulation of presynaptic $\alpha_2$-adrenergic receptors. However, the lowering of blood pressure by these agents is not related to stimulation of these receptors, but rather to postsynaptic adrenergic receptors (Birch et al., Br. J. Pharmacol., 68, 107P (1979)). Accordingly, selective $\alpha_2$-receptor antagonists are useful in reducing the adverse effect of sedation produced by antihypertensive drugs. Thus, the selective $\alpha_2$-receptor blocker, yohimbine, antagonizes the sedation produced by clonidine (Drew et al., Br. J. Pharmacol., 67, 133 (1979)) and the locomotor depressant effects of methyldopa in rats (Clineschmidt et al., Arch. Int. Pharmacodyn. Ther., 244, 231 (1980)). In addition, yohimbine has been reported to reduce clonidine-induced sedation in man (Autret et al., Eur. J. Clin. Pharmacol., 12, 319 (1977)).

The compounds useful in the novel method of treatment of the present invention, being highly selective for the $\alpha_2$-adrenergic receptor, effectively reduce the sedative effects of antihypertensive agents without affecting the blood pressure lowering properties. Combinations of antihypertensive agents with selective $\alpha_2$-adrenergic receptor antagonists form an additional aspect of this invention.

DETAILED DESCRIPTION OF THE INVENTION

This invention is concerned with the use of a compound which selectively antagonizes $\alpha_2$-adrenergic receptors in the treatment of sedation caused by antihypertensive drug therapy, wherein the compound is of structural formula:

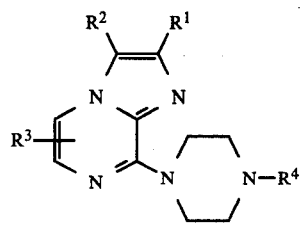

or a pharmaceutically acceptable salt thereof, wherein $R^1$, $R^2$ and $R^3$ are independently hydrogen or halogen such as chloro, or fluoro; and $R^4$ is hydrogen or $C_{1-3}$ alkyl. Preferably, $R^1$, $R^2$, $R^3$ and $R^4$ are all hydrogen.

The pharmaceutically acceptable salts are those resulting from the neutralization of the base with an acid. The acid employed is usually an inorganic acid such as a hydrohalic acid such as hydrochloric or hydrobromic acid; sulfuric acid; nitric acid; or phosphoric acid. An organic acid such as maleic, fumaric, tartaric, citric, acetic, salicylic, succinic, benzoic, benzenesulfonic, glutamic, lactic or isethionic acid is also commonly used.

Compounds of structural formula I and its pharmaceutically acceptable salts are disclosed in U.S. Pat. No. 4,242,344 and its disclosure is incorporated herein by reference.

In the novel method of treating sedation caused by antihypertensive drug therapy in a patient, an active compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

The compounds, or pharmaceutically acceptable salts thereof, of the present invention, in the described dosages, are administered orally, intraperitoneally, subcutaneously, intramuscularly, or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

It is convenient to formulate the active compound in combination with an antihypertensive agent such as methyldopa. In such combinations the antihypertensive agent is present in amounts normally employed for antihypertensive therapy.

EXAMPLE 1

Adrenergic Receptor Binding Assays for 8-(1-piperazinyl)imidazo[1,2-a]pyrazine and Derivatives The $\alpha_1$- and $\alpha_2$-adrenergic receptor binding as determined for some of the active compounds of this invention are shown in Table I.

Extent of binding to the $\alpha_1$-adrenergic receptor was determined by the method of Greengrass and Bremner, Eur. J. Pharmacol., 55, 323 (1979) and is expressed in Table I as Ki, representing the affinity of each compound for the [$^3$H] prazosin binding site in calf cerebral cortex.

Binding to the $\alpha_2$-adrenergic receptor was determined by the method of Lyon and Randall, *Life Sciences*, 26, 1121 (1980) and also is expressed in Table I as Ki representing the affinity of each compound for the [$^3$H] clonidine binding site in calf cerebral cortex.

TABLE I

Adrenergic Receptor Binding of 8-(1-piperazinyl)imidazo-[1,2-a]pyrazine and derivatives

| Compound | R$^1$ | R$^2$ | R$^3$ | R$^4$ | Adrenergic Binding Ki(nM) $\alpha_2$ | $\alpha_1$ |
|---|---|---|---|---|---|---|
| 1 | H | H | 6-Cl | H | 73.0 | 250 |
| 2 | H | Cl | H | H | 240 | 2800 |
| 3 | H | H | H | H | 15 | 3100 |
| 4 | H | H | 6-Cl | CH$_3$ | 121 | 380 |

Clearly the compounds of the novel method of treatment of this invention have strong affinity (low Ki), for the $\alpha_2$-adrenergic receptors and weak affinity (high Ki) for the $\alpha_1$-adrenergic receptors.

EXAMPLE 2

8-(1-Piperazinyl)imidazo[1,2-a]Pyrazine Dihydrochloride Hydrate Antagonism of $\alpha$-Methyldopa ($\alpha$-MD) Depression of Rat Locomotor Activity Female Sprague-Dawley rats (Sprague-Dawley, Madison, Wis.) weighing 55-90 g were used in these studies. The test apparatus consisted of 10 activity chambers in a closed metal cabinet separated into individual compartments measuring 43×43 cm with a solid partition between each chamber. Ventilation in the cabinet was provided by two high speed fans, and background noise was supplied with a Grason-Stadler Noise Generator. The activity chambers were constructed from clear plexiglass cylinders, 30 cm high by 30 cm in diameter. Two infrared photocells were mounted at a height of 3 cm above the floor, the receivers being at the same height and directly opposite. Interruption of either of the beams registered independently as an activity count. The accumulated locomotor activity counts were stored in a microprocessor-based acquisition system and printed out at a preprogrammed interval on an ASR-33 Teletype unit. The decrease in locomotor activity caused by $\alpha$-MD is most readily demonstrable during the time immediately following introduction of the rats into the test apparatus. Therefore, activity counts were recorded for a 20-minute period, beginning with placement of the animals in the test chambers. Animals with the various treatments were systematically rotated through the chambers. Data from the locomotor activity studies were transformed into the square roots of the counts prior to statistical evaluation, since the frequency distribution of the activity counts was found to be skewed in the positive direction, i.e., higher counts being further away from the mean than lower counts. Dunnett's test was used for comparison of several treatment groups with a control group and the least significant difference test for comparison of the means of any two treatment groups. A P value of 0.05 (two-sided) was considered as indicating significance.

Animals were pretreated (3 hours, 4 minutes) with $\alpha$-MD (200 or 400 mg/kg, p.o.), and various doses of 8-(1-piperazinyl)imidazo[1,2-a]pyrazine.2HCl.H$_2$O (0.11-3.0 mg/kg, sc) 40 minutes prior to testing. Vehicles used in control animals were 1% methylcellulose (in which $\alpha$-MD was suspended) and saline (in which the experimental compound was dissolved). The results are shown in Table II

TABLE II

| Treatment 1  3 hr. (mg/kg p.o.) | Treatment 2  40 min. (mg/kg s.c.) | Activity Counts (0-20 min) $\sqrt{x} \pm$ SEM |
|---|---|---|
| 1. Methylcellulose | Saline | 13.3 ± 1.5 |
| $\alpha$-MD (400) | Saline | 4.7 ± 0.7 |
| $\alpha$-MD (400) | Compound (3) | 11.6 ± 1.3 |
| $\alpha$-MD (400) | Compound (1.0) | 11.7 ± 1.3 |
| $\alpha$-MD (400) | Compound (0.33) | 8.4 ± 0.9 |
| $\alpha$-MD (400) | Compound (0.11) | 5.1 ± 0.5 |
| 2. Methylcellulose | Saline | 12.9 ± 1.2 |
| $\alpha$-MD (200) | Saline | 6.8 ± 0.5 |
| $\alpha$-MD (200) | Compound (3.0) | 12.2 ± 1.2 |
| $\alpha$-MD (200) | Compound (1.0) | 11.4 ± 1.2 |
| $\alpha$-MD (200) | Compound (0.33) | 9.5 ± 1.2 |
| $\alpha$-MD (200) | Compound (0.11) | 8.4 ± 1.1 |

P 0.05 vs Vehicle
P 0.05 vs $\alpha$-MD + Saline

EXAMPLE 3

Pharmaceutical Formulation

| Ingredient | Mg/Capsule |
|---|---|
| 8-(1-piperazinyl)imidazo[1,2-a]-pyrazine dihydrochloride hydrate | 6 |
| starch | 87 |
| magnesium stearate | 7 |

The active ingredient, starch and magnesium stearate are blended together. The mixture is used to fill hard shell capsules of a suitable size at a fill weight of 100 mg per capsule.

EXAMPLE 4

Pharmaceutical Formulation—including an antihypertensive Agent

| Ingredients | Mg/Capsule |
|---|---|
| 8-(1-piperazinyl)imidazo[1,2-a]pyrazine dihydrochloride hydrate | 6 |
| methyldopa | 250 |
| starch | 219 |
| magnesium stearate | 25 |

The active ingredients, starch and magnesium stearate are blended together. The mixture is used to fill hard shell capsules of a suitable size at a fill weight of 500 mg per capsule.

What is claimed is:

1. A method of treating sedation caused by antihypertensive drug therapy through stimulation of presynaptic $\alpha_2$-adrenergic receptors in a patient in need of such treatment which comprises the administration of 0.01-20 mg/kg/day of a compound of structural formula:

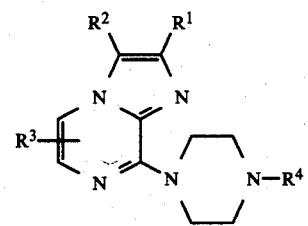

or a pharmaceutically acceptable salt thereof, wherein $R^1$, $R^2$ and $R^3$ are independently hydrogen or halogen; and $R^4$ is hydrogen or $C_{1-3}$alkyl.

2. The method of claim 1, wherein $R^4$ is hydrogen or methyl.

3. The method of claim 1, wherein the compound is 8-(1-piperazinyl)imidazo[1,2-a]pyrazine.

4. A pharmaceutical composition for treating hypertension and sedation caused thereby which comprises a pharmaceutical carrier, an effective amount of an antihypertensive agent known to cause sedation through stimulation of presynaptic $\alpha_2$-adrenergic receptors and an amount of a compound to provide a dosage of 0.01–20 mg/kg/day wherein the compounds has structural formula:

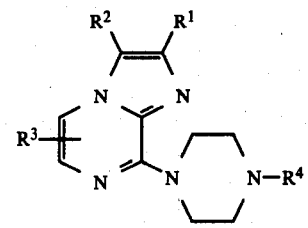

or a pharmaceutically acceptable salt thereof, wherein $R^1$, $R^2$ and $R^3$ are independently hydrogen or halogen; and $R^4$ is hydrogen or $C_{1-3}$alkyl.

5. The formulation of claim 4, wherein $R^4$ is hydrogen or methyl.

6. The formulation of claim 4, wherein the antisedative compound is 8-(1-piperazinyl)imidazo[1,2-a]pyrazine.

7. The formulation of claims 4, 5 or 6 wherein the antihypertensive agent is methyldopa.

* * * * *